United States Patent [19]

Mann et al.

[11] Patent Number: 4,864,150

[45] Date of Patent: Sep. 5, 1989

[54] METHOD FOR INSPECTING, DETECTING AND DISTINGUISHING SIDES OF FABRICS

[75] Inventors: Michael G. Mann, Jackson's Gap; John P. Graves, Alexander City, both of Ala.

[73] Assignee: Russell Corporation, Alexander City, Ala.

[21] Appl. No.: 154,642

[22] Filed: Feb. 9, 1988

[51] Int. Cl.$^4$ .......................... G01N 21/86; G01V 9/04
[52] U.S. Cl. ........................................ 250/571; 356/429
[58] Field of Search ............... 250/559, 571, 562, 563, 250/341, 358.1, 359.1; 356/238, 429, 445, 446, 447, 448

[56] References Cited

U.S. PATENT DOCUMENTS

| 3,474,254 | 10/1969 | Piepenbrink et al. | 356/238 |
| 4,306,151 | 12/1981 | Chase | 250/341 |
| 4,750,140 | 6/1988 | Asano et al. | 356/445 |

Primary Examiner—David C. Nelms
Assistant Examiner—Eric F. Chatmon
Attorney, Agent, or Firm—Thad G. Long

[57] ABSTRACT

A method for inspecting, detecting and distinguishing sides of fabrics by reflecting light off the fabric and measuring the intensities relatively or absolutely, of such reflected light and comparing such measurements with pre-determined calibrations or other appropriate standards of comparison, so that the fabric can be properly oriented for sewing like sides to like sides, relying on different light reflecting characteristics of the two sides of the fabric.

32 Claims, 9 Drawing Sheets

METHOD FOR INSPECTING, DETECTING AND DISTINGUISHING SIDES OF FABRICS

BRIEF SUMMARY OF THE INVENTION

It is a characteristic of woven fabrics that the two sides of a given fabric frequently, if not invariably, differ from each other in texture, dominance of thread directions, and appearance. This is especially true of fabrics made of natural materials such as cotton, wool and linen. In sewing separate pieces of fabric together to form a garment, it is normally desirable and expected by consumers that the outer side of the finished garment have a substantially uniform appearance and texture, except for color and other intentional variations in decoration of the garment.

Typically, garment makers utilize the smoother and more "finished" fabric side to form the outer portion of garments while the somewhat rougher and sometimes slightly "fuzzy" side is used for the inner portion. Sometimes, for special effects, a garment maker may intentionally reverse the above norm in producing particular garments. In either case, the garment maker will usually want to sew together the individual pieces of fabric in such a manner that all the fabric in the finished garment is consistently oriented so that each side will have consistent texture, dominance of thread direction and appearance.

When garments are manually sewed, it is usually not difficult for the human sewer to distinguish the different sides of separate pieces of fabrics so as to sew them together correctly, like side to like side. However, in mechanized and automated garment manufacture, it has been a difficult technical problem as to how to insure that like sides are sewn together consistently.

If wrong sides are inadvertently sewn together, the expense of undoing the incorrect sewing and resewing the fabric pieces correctly is usually prohibitively expensive, especially for relatively low-priced goods such as T-shirts. Consequently, incorrectly sewed garments are usually wasted. The waste and the cost burden on the overall manufacturing operation can be substantial when entire stacks of fabric pieces are sewed together incorrectly.

In the manufacturing process, fabric pieces are normally fed sequentially from different stacking points to a central location where two or more pieces of fabric are sewed together. Obviously, one of the standard means for attempting to guard against incorrect sides being sewed together is to stack the fabric pieces correctly and consistently at the respective stacking points, before they are sequentially fed together for sewing. However, it is nearly impossible to prevent such missewing by proper stacking, for several reasons. It is not feasible in a high volume, automated garment manufacturing operation to visually inspect each fabric piece in a stack to insure that it is correctly oriented with respect to side. Furthermore, human stacking errors and human inspection errors must be anticipated in any event.

No reliable method has heretofore been found, so far as we are aware, for high speed inspection of fabric sides in a garment manufacturing operation which will enable the manufacturer to take corrective action before fabric pieces are incorrectly sewed together.

An object of the present invention is to provide a method for inspecting fabrics or fabric pieces, especially in an automated manufacturing context, and for providing a method for detecting and distinguishing the two different sides of the fabrics or fabric pieces. Another object of the invention is to provide differing output signals which correspond with the different sides of fabrics or fabric pieces so that such signals can then alert assembly-line operators so that they can in turn correct an improperly oriented fabric piece on the assembly line or, alternatively and preferably, activate a device for passing or flipping the fabric piece for correct orientation prior to sewing.

The present invention makes use of the fact that directional patterns of threads predominate in fabrics, which patterns are different, depending on the fabric side. On one side the thread patterns will predominate in one direction, while on the reverse side the predominant thread patterns will run at a 90° angle thereto. When fabric lies in a plane and light is transmitted to the fabric surface at an oblique angle to the surface, greater or lesser amounts of light will be reflected back toward the emitting source, depending upon which side of the fabric has been "hit" by the transmitted light. Because the same side of the fabric will produce substantially the same intensities of reflected light for a given set of conditions (within a reasonable range) and because the opposite side of the fabric will produce a distinguishable range of intensities of reflected light for a given set of conditions, it is possible to calibrate one or more sensors which measure the intensities of reflected light so as to distinguish the different sides in various ways, some of which will be described below.

DETAILED DESCRIPTION OF THE DRAWINGS

Figure 1:
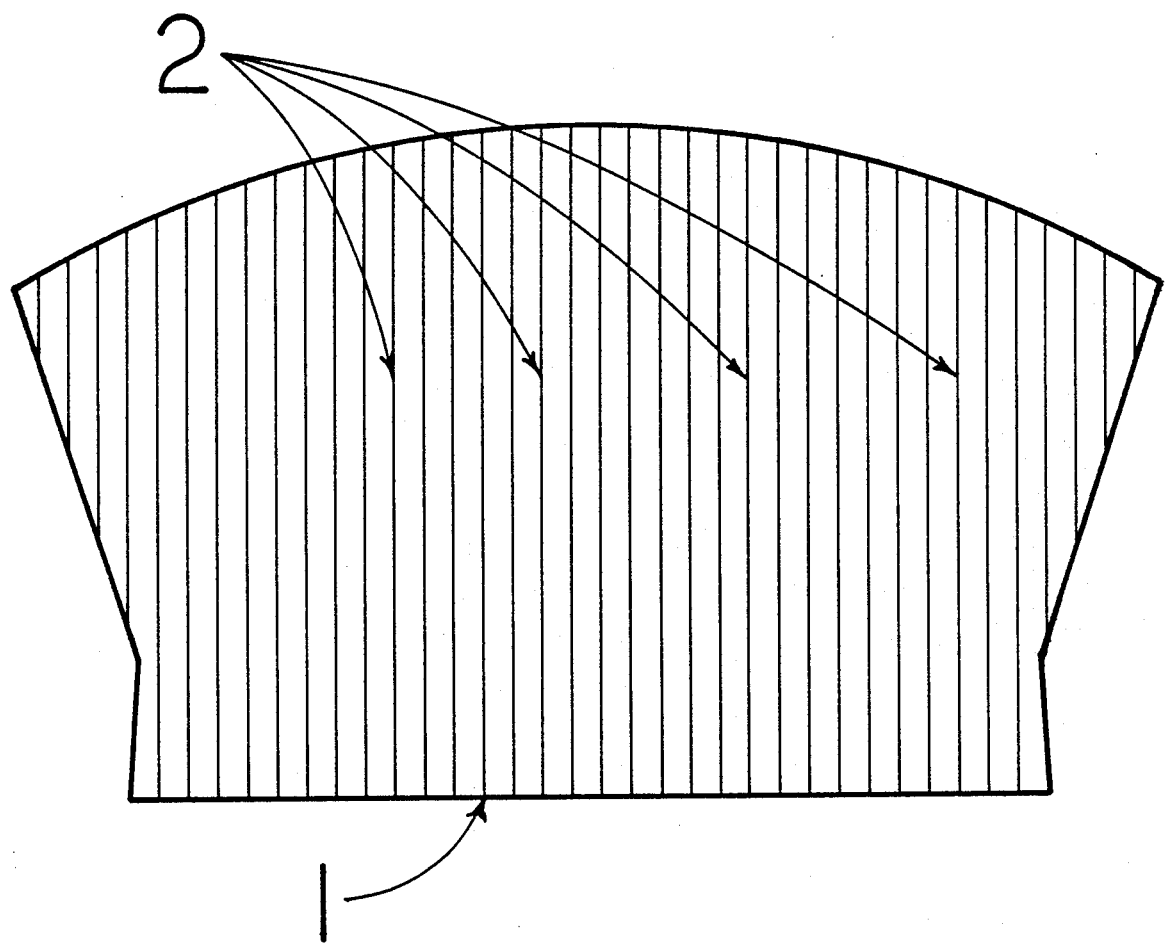
FIG. 1 is a schematic drawing showing dominant thread patterns of one side of a fabric piece, which for convenience is designated herein as the "face" side.

In FIG. 1, there is shown a schematic diagram of a fabric piece 1, in this case a T-shirt sleeve, face side up. There is shown on the face of fabric piece 1 an exaggerated illustration of the dominant thread lines 2 running vertically on the drawing.

Figure 2:
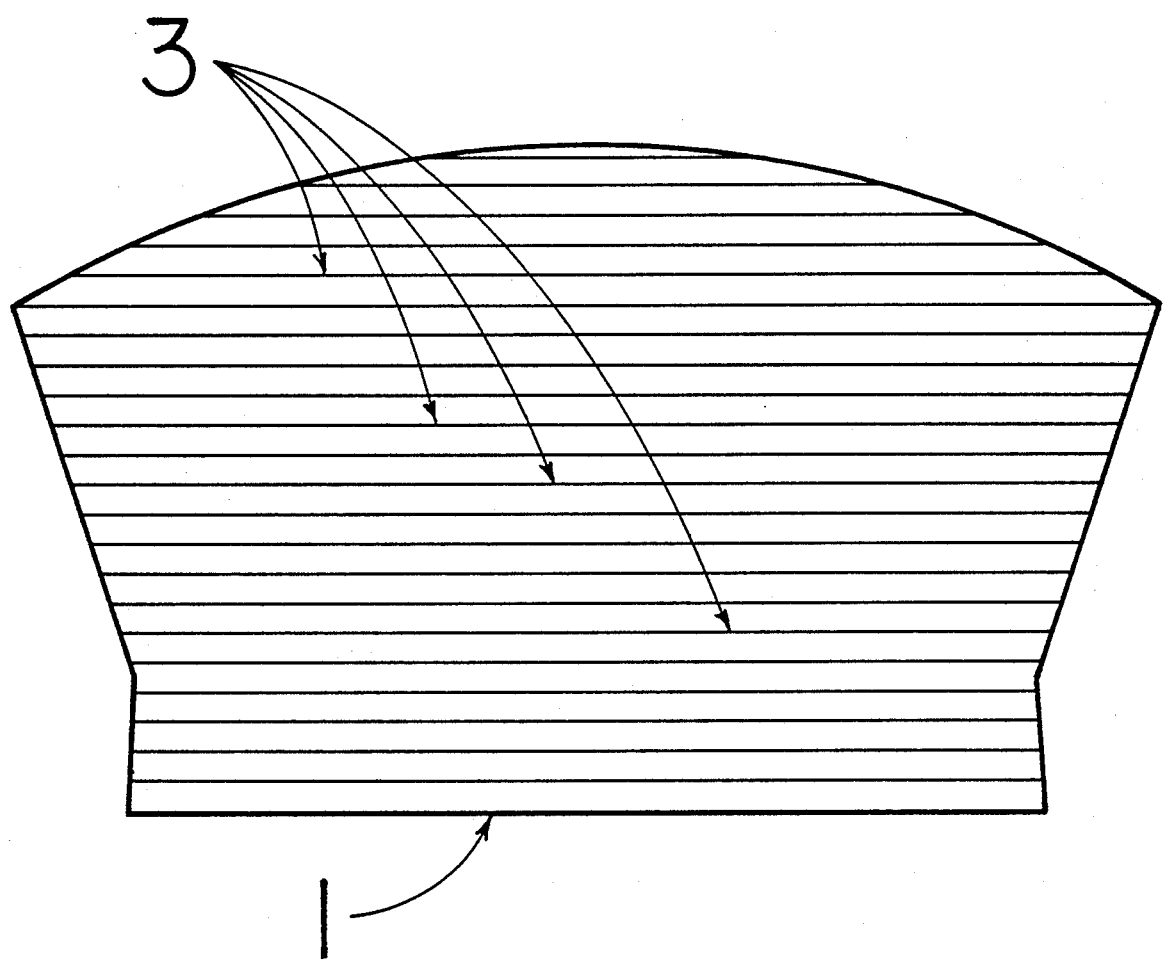
FIG. 2 is a schematic drawing showing dominant thread patterns of the reverse of the "face" side of the fabric price, which for convenience is designated herein on the "back" side.

In FIG. 2, there is shown a schematic diagram of the back side of the same fabric piece 1. There is shown on the back of fabric piece 1 an exaggerated illustration of the dominant thread lines 3 running horizontally on the drawing.

Figure 3:
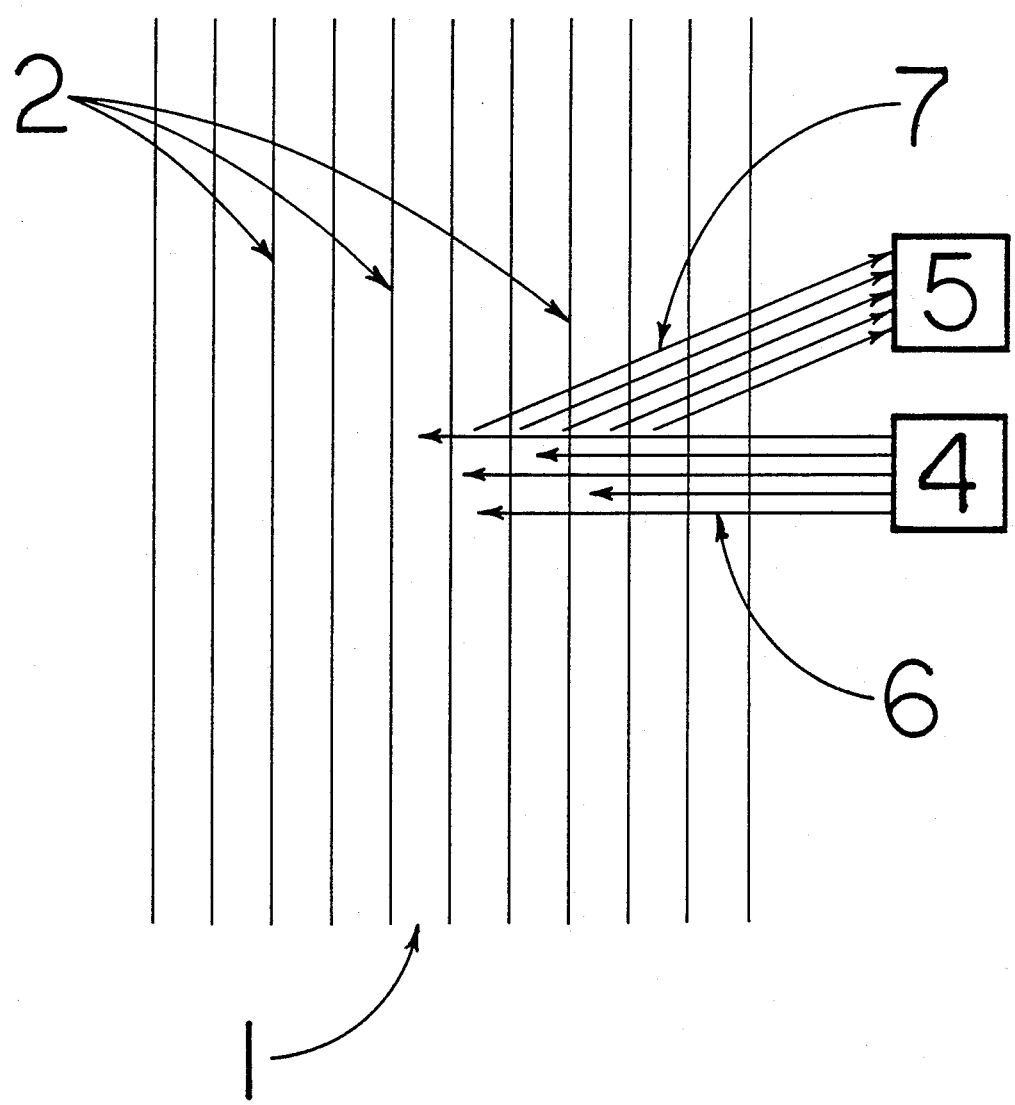
FIG. 3 is a schematic drawing showing a light source transmitting light to the face side of fabric, at an oblique angle relative to the surface of the face side of the fabric, with a light sensor located in general proximity to the light source so as to measure the intensity of the light reflected off the face of the fabric.

FIG. 3 shows a segment of the face side of fabric piece 1, showing a light source 4 transmitting light rays 6 at an oblique angle onto the surface of the face side of the fabric piece 1 and perpendicularly to the exaggerated illustration of the dominant thread lines 2. There is also shown a sensor 5 located in general proximity to light source 4 and on the same side of the segment of the fabric piece 1 as light source 4. When light rays 6 are emitted from light source 4, some of the rays 7 are reflected back to the sensor 5 which can measure the intensity of the reflected rays 7. The intensity of the reflected light rays 7 can thus be compared with the known intensity of light rays 6 which were emitted initially. The intensity of light rays 6 will vary, depending upon the particular oblique angle used for transmitting light to the face surface of fabric piece 1 and depending upon the type of fabric. However, for a given type of fabric and a given oblique angle, it will be possible to determine a reasonably narrow range of intensities of reflected light rays 7 which can be expected to result from transmitting light rays 6 to the face side of the fabric and reflecting some of the light rays 7 back to the sensor 5.

Figure 4:
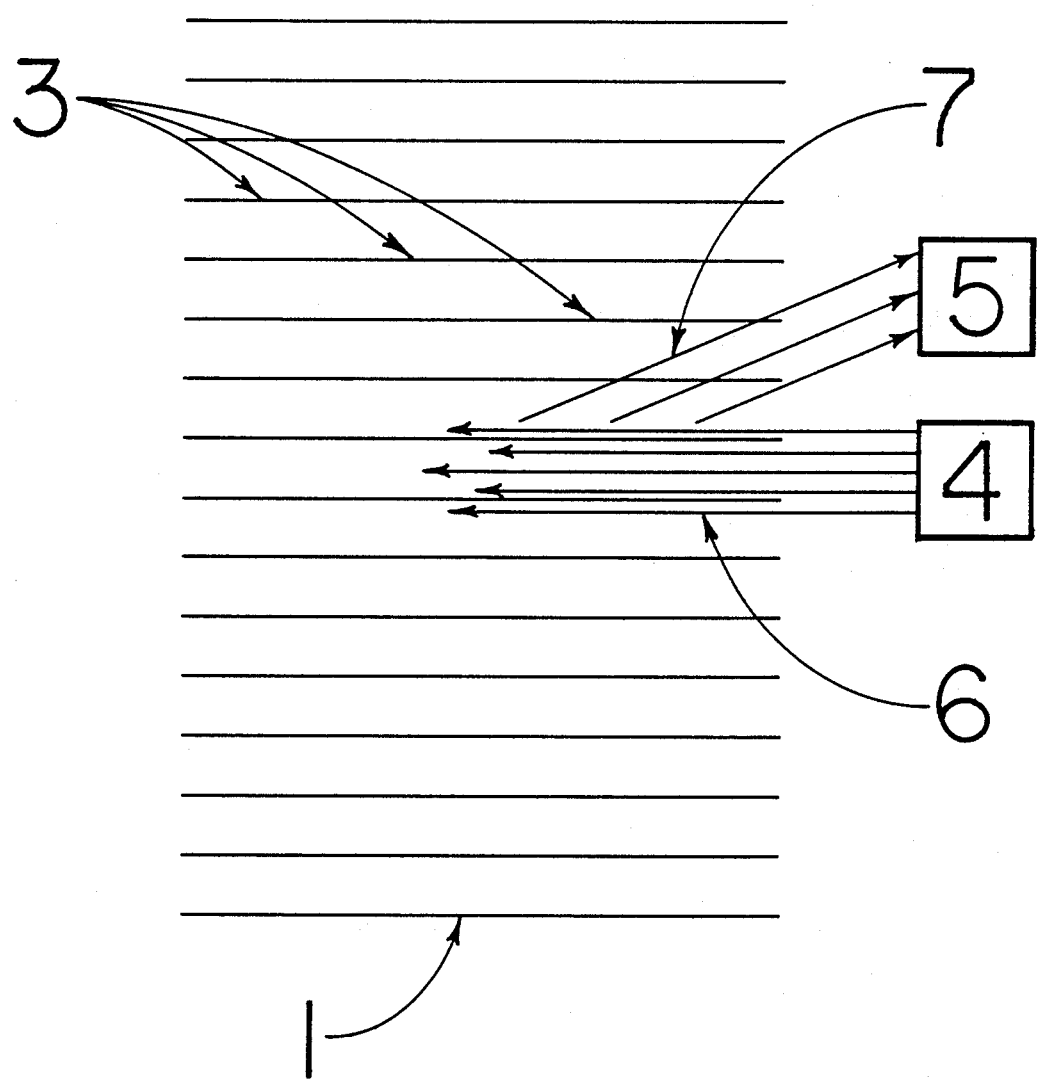
FIG. 4 is a schematic drawing showing a light source transmitting light to the back side of fabric at an oblique angle relative to the surface of the back side of the fabric, with a light sensor located in general proximity to the light source so as to measure the intensity of the light reflected off the back side of the fabric.

FIG. 4 shows a segment of the back side of fabric piece 1, showing a light source 4 transmitting light rays 6 at an oblique angle onto the surface of the back and parallel to the exaggerated illustration of the dominant thread lines 3. There is also shown a sensor 5 located in general proximity to light source 4 and on the same side of the segment of fabric piece 1 as light source 4. When light rays 6 are emitted from light source 4, some of the rays 7 are reflected back to the sensor 5 which can measure the intensity of the reflected light rays 7. The intensity of the reflected light rays 7 can thus be compared with the known intensity of light rays 6 which were emitted initially. The intensity of light rays 7 will vary, depending upon the particular oblique angle used for transmitting light to the back surface of fabric piece 1 and depending upon the type of fabric. However, for a given type of fabric and a given oblique angle, it will be possible to determine a reasonably narrow range of intensities of reflected light rays 7 which can be expected to result from transmitting light rays 6 to the back side of the fabric and reflecting some of the light rays 7 back to the sensor 5.

Very significantly, it is found that, under otherwise constant conditions, the intensity of reflected light rays 7 from the back side of the segment of fabric piece 1 as shown in FIG. 4 is always substantially less than the intensity of reflected light rays 7 from the face side of the segment of fabric piece 1 as shown in FIG. 3. It is this basic principle which enables one to inspect and distinguish face and back sides of fabric pieces by means of light sources and sensors and, having distinguished the sides, to provide the necessary computerized output to activate a device for flipping or passing the fabric pieces so as to insure that all fabric pieces reaching a central sewing location have the same side orientation, or otherwise effectuate uniformity of side orientation for fabric pieces.

Figure 5:
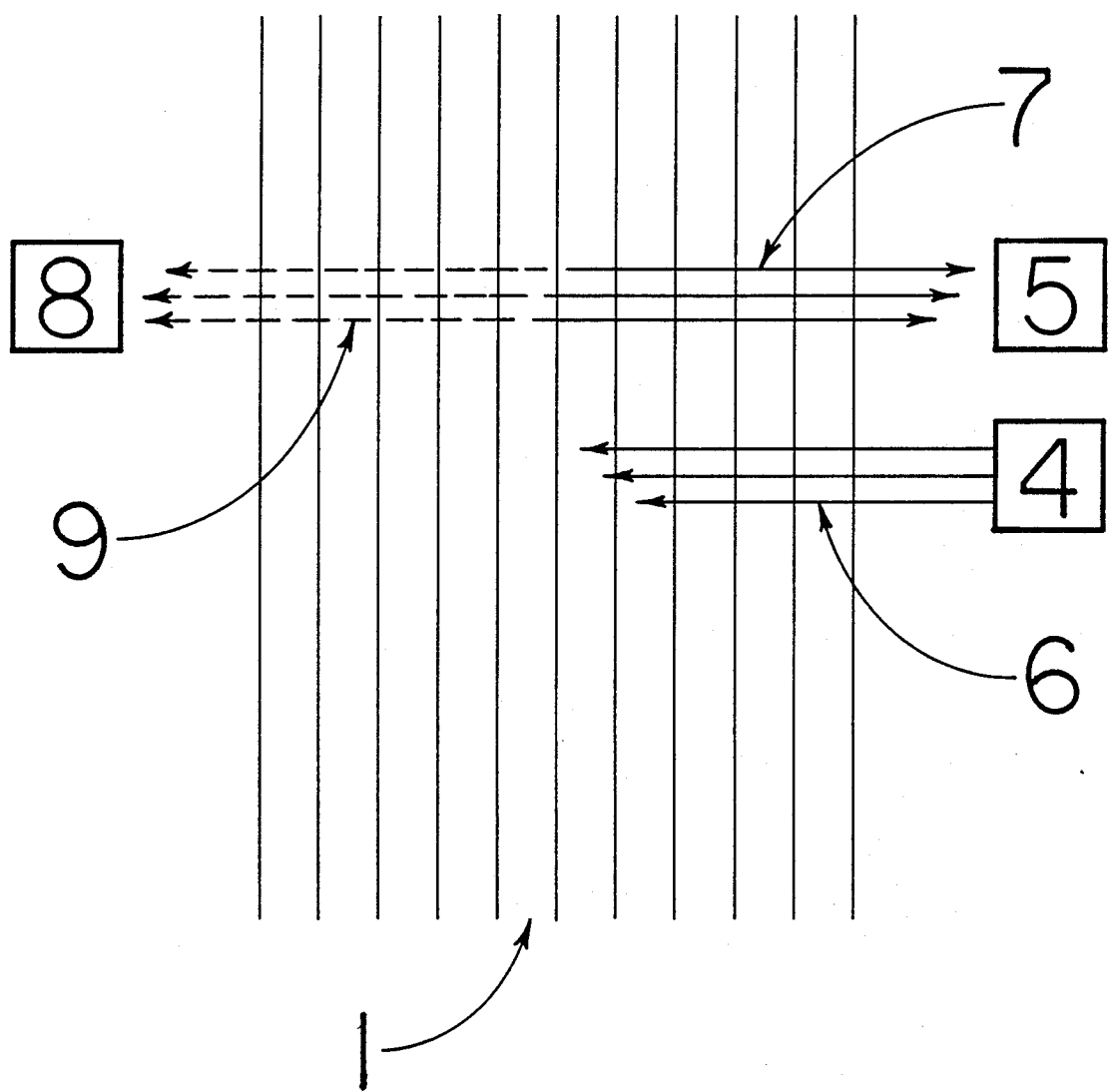
FIG. 5 is a schematic drawing similar to FIG. 3, except that there has been added an additional sensor opposite the light source and first sensor.

FIG. 5 is similar to FIG. 3, except that in FIG. 5 there has been added a second sensor 8 on a side of the segment of fabric piece 1 opposite light source 4 and first sensor 5. Under this configuration, there of course continue to be light rays 7 reflected back to sensor 5. However, there are also light rays 9 which reflect off the surface of the face side of fabric piece 1 to the second sensor 8. The intensity of the light rays 9 can be measured by sensor 8 and compared with the known intensity of light rays 6 which were emitted initially. The intensity of light rays 9 will vary, depending upon the particular oblique angle used for transmitting light to the face surface of fabric piece 1 and depending upon the type of fabric. However, for a given type of fabric and a given oblique angle, it will be possible to determine a reasonably narrow range of intensities of reflected light rays 9 which can be expected to result from transmitting light rays 6 to the face side of the fabrics and then reflecting some of the light rays 9 to second sensor 8. Very significantly, it is found that under otherwise constant conditions, the intensity of reflected light rays 9 as measured on sensor 8 is always substantially less than the intensity of reflected light rays 7 as measured by sensor 5. By arranging two sensors 5 and 8, as shown in FIG. 5, it is possible to have a double check on whether the fabric being inspected is face side up or back side up. This double check improves reliability of the process of inspecting and distinguishing fabric sides, by minimizing errors due to a malfunctioning sensor. Obviously, even more sensors could be used, if desired.

Figure 6:
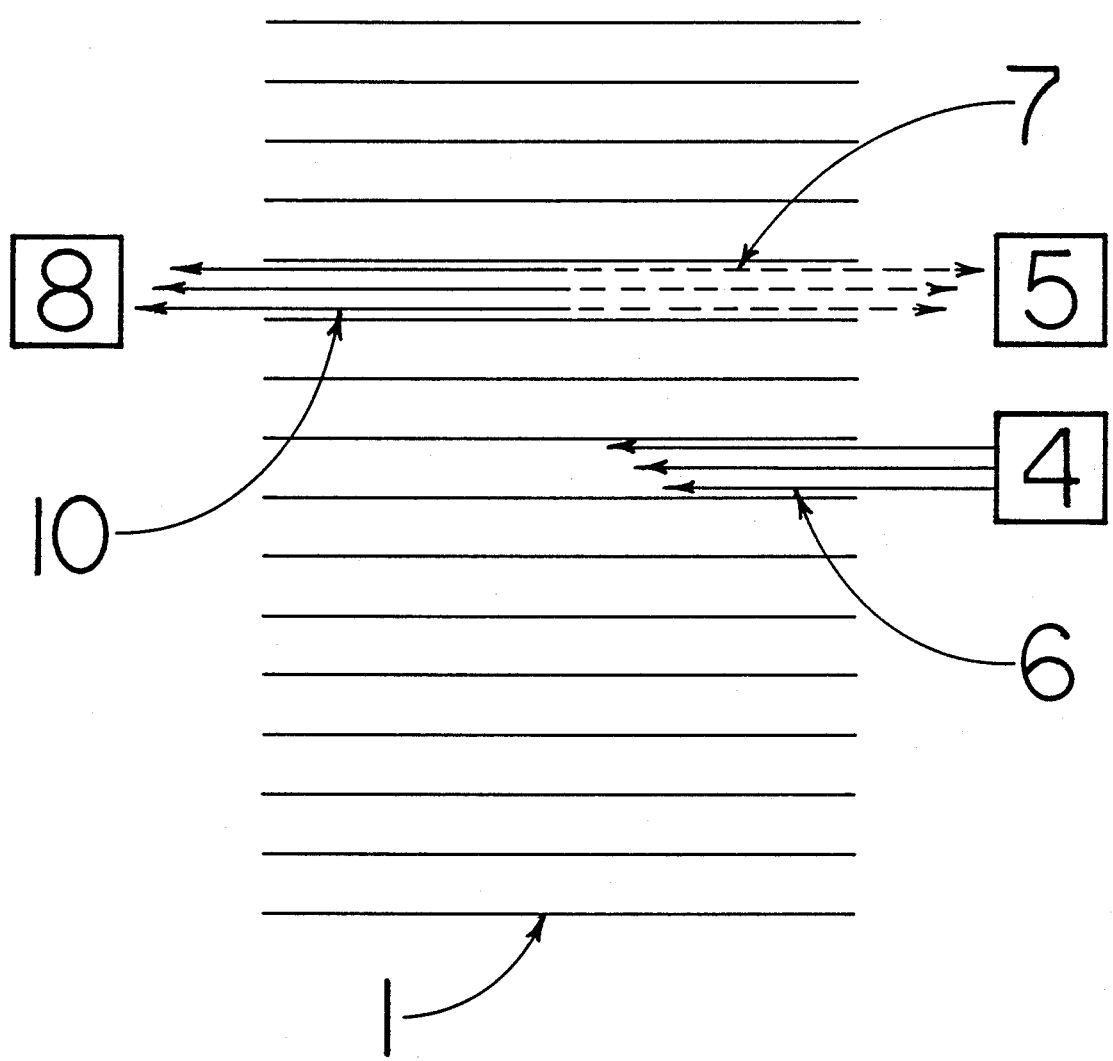
FIG. 6 is a schematic drawing similar to FIG. 4, except that there has been added an additional sensor opposite the light source and first sensor.

FIG. 6 is similar to FIG. 4, except that in FIG. 6 there has been added a second sensor 8 on a side of the segment of fabric piece 1 opposite light source 4 and first sensor 5. Under this configuration, there of course continue to be light rays 7 reflected back to sensor 5. However, there are also light rays 10 which reflect off the surface of the back side of fabric piece 1 to the second sensor 8. The intensity of the reflected light rays 10 can be measured by sensor 8 and compared with the known intensity of light rays 6 which were emitted initially. The intensity of light rays 10 will vary, depending upon the particular oblique angle used for transmitting light to the back surface of fabric piece 1 and depending upon the type of fabric. However, for a given type of fabric and a given oblique angle, it will be possible to determine a reasonably narrow range of intensities of reflected light rays 10 which can be expected to result from transmitting light rays 6 to the back side of the fabric and then reflecting some of the light rays 10 to second sensor 8. Very significantly, it is found that, under otherwise constant conditions, the intensity of reflected light rays 10 as measured on sensor 8 is always substantially greater than the intensity of reflected light rays 7 as measured by sensor 5. This is precisely opposite the result obtained under the same conditions for the face side of the fabric where, as noted above in the discussion of FIG. 5, sensor 5 measures a greater intensity of reflected light than sensor 8. By arranging two sensors 5 and 8, as shown in FIG. 6, it is possible to have a double check on whether the fabric being inspected is face side up or back side up. This double check improves reliability of the process of inspecting and distinguishing fabric sides, by minimizing errors due to a malfunctioning sensor. Obviously, even more sensors could be used, if desired.

Figure 7:
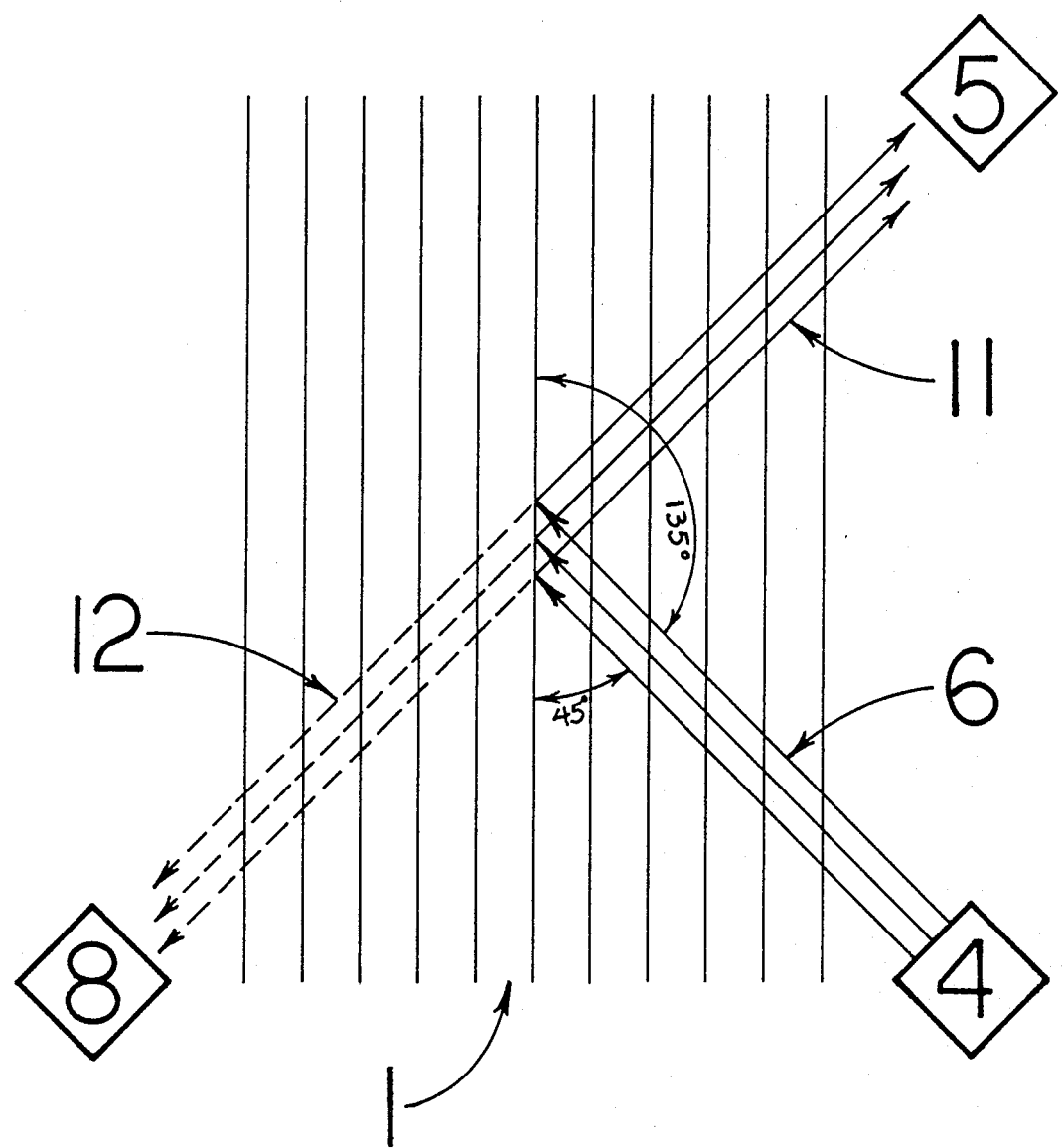
FIG. 7 is a schematic drawing showing a light source transmitting light obliquely relative to the surface of the fabric and at a 45° angle relative to the directional run of the dominant thread pattern on the face of the fabric, and with two sensors located opposite each other on a line perpendicular to the direction of light transmitted.

FIG. 7 shows light source 4 transmitting light obliquely to the surface of the face side of a segment of fabric piece 1 but at an approximately 45° (or 135°) angle to the directional run of the dominant thread patterns on the face of the fabric piece 1. The sensors 5 and 8 have been placed so as to face each other on opposite sides of the said fabric segment on a line that is perpendicular to the direction of transmission of light rays 6 from light source 4. Certain light rays 11 are reflected toward sensor 5 (on the same side of the said fabric segment as light source 4) and certain light rays 12 are reflected toward sensor 8. The intensity of the reflected light rays 11 and 12 can be measured by sensors 5 and 8, respectively, and can be compared with the known intensity of light rays 6 which were emitted initially. The intensities of the light rays 11 and 12 as measured by the respective sensors will vary, depending upon the particular oblique angle used for transmitting light to the face surface of fabric piece 1 and depending upon the type of fabric. However, for a given type of fabric and a given oblique angle, it will be possible to determine reasonably narrow respective ranges of intensities of reflected light rays 11 and 12. Very significantly, sensor 5 will always measure a substantially higher intensity for light rays 11 than sensor 8 will measure for light rays 12. Indeed, sensor 5 will register higher intensities than sensor 8 if fabric segment 1 is rotated in its plane in any direction up to but less than 45°. Thus, the differential in measured intensities between sensors 5 and 8 provides a reliable means of distinguishing the face and back sides of fabrics for a wide range of angles less than 90°. Of course, by relying on calibrations under specific conditions, it would be possible to distinguish between face and back sides of fabrics by using only one sensor, 5 or 8. However, reliability is improved by use of two or more sensors. Clearly, the sensors do not necessarily have to be pointed at a 90° angle to the direction of transmission of light rays from light source 4. Changing the angular direction of the sensors relative to the path of transmission of light rays from light source 4 would change the intensities measured, but it would still be possible to calibrate the sensors so that under other constant conditions face sides of fabrics could be distinguished from back sides.

Figure 8:
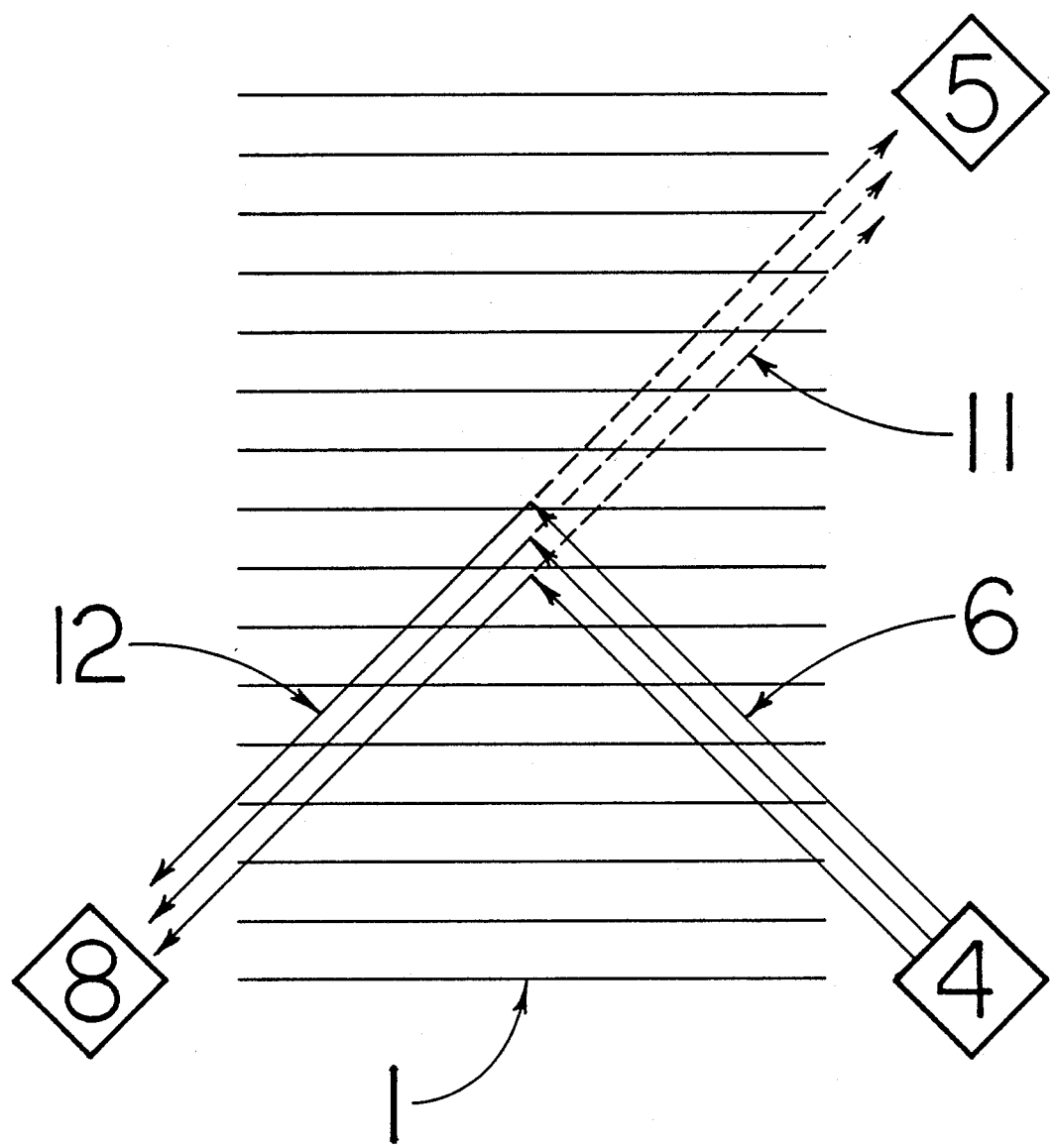
FIG. 8 is a schematic diagram similar to FIG. 7 except the light source is directed at the back of the fabric.
Figure 9:
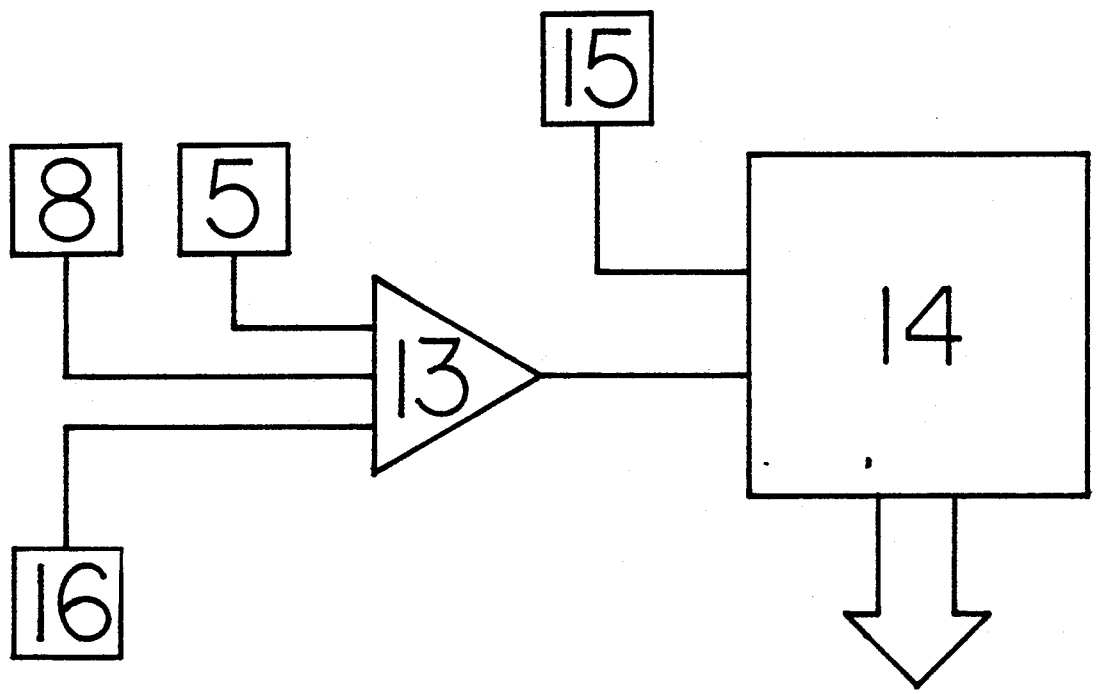
FIG. 9 is a schematic diagram showing the use of a comparator which receives reading from the sensors, makes appropriate comparisons and then transmits a signal to a programable controller which analyzes the input and controls devices for passing or flipping the fabric.

FIG. 8 is the same as FIG. 7 except that the back side of the segment of fabric piece 1 is the surface to which light rays 6 are transmitted and from which light rays 11 and 12 are reflected respectively to sensors 5 and 8. It will be seen that in FIG. 8 the directional run of the dominant thread patterns is horizontal (as shown), which is 90° different from FIG. 7. As a consequence, the results here are reversed. It is sensor 8 measuring light rays 12 which shows the higher intensities and sensor 5 measuring light rays 11 which shows lower intensities. All observations made with respect to FIG. 7 apply also to FIG. 8 but with the conclusions reversed as to light rays 11 and 12 and sensors 5 and 8.

As used in the specification and claims herein, the word "light" means any electromagnetic wave with wave lengths in the range of infrared, visible, ultraviolet, and x-ray spectra. However, when the method herein discussed is used in a commercial manufacturing facility, it is found that modulated infrared light is most practical because there are generally too many light sources and too much light in the visible spectrum and at certain other wavelengths to isolate the light emitted from light source 4 so that reflections thereof can be accurately measured without also measuring light reflected from extraneous sources. The sensors are designed or set in such manner as to disregard all non-modulated light, which includes the ambient light in the area.

Furthermore, while the light rays 6 can be transmitted to the surface of fabric pieces at any oblique angle, it is found that angles of 30° to 60° work best. At angles approaching 0°, minor wrinkles in the fabric piece and other distorting influences may affect the accuracy and reliability of readings. The same is true as angles approach 90°.

In general, it is found that wrinkles, rumples and other nonplanar configurations of the fabric being inspected do affect the reliability and accuracy of the method set forth herein, when single, isolated readings are taken. However, the possibility of error is reduced as increasingly larger numbers of reading are taken at different places on the surface of the fabric and the predominance of readings is used as the determiner of fabric side. A comparator or computer or similar electronic device can be used to analyze such multiple readings and ascertain predominance from among such multiple readings. It is found that a high degree of reliability is obtained when 50 or more readings are taken at different points on a piece of fabric. Such readings can be rapidly done, nearly instantaneously or in any event within the few seconds that a piece of fabric may be passing in the vicinity of the light source and sensor. Similarly, such readings can be very rapidly analyzed and compared by the equipment being used for the purpose. When the predominant reading is selected by such equipment, the side determination is thereby made and the corresponding output signal is sent to activate the mechanism for passing or flipping the fabric, or an audible or visible fabric side indicator is activated so as to alert a human operator as to the side facing up, so that such operator can manually flip (or by inaction pass) the piece of fabric to the next position.

An analog photo-electric eye can be used as an appropriate sensor, and a photo-electric transmitter can be used as a light source.

Obviously, there are many other ways that calibrations or comparative light intensity readings can be used to distinguish the face side and the back side of a fabric piece using the method herein described and claimed, and those which are specifically discussed herein are only particular examples used by way of illustration. Another example, not discussed in detail, would be comparing light intensity readings from both sides of the fabric piece, through open spaces in the conveying system designed to facilitate light intensity measurements taken from the under side of the fabric piece, as well as the top side.

The comparator has adjustable thresholds which can be set manually through adjustment module 16 (based on calibrations theretofore made from samples of fabric pieces to be inspect-ed, and at specific angles to be used for transmitting light from a light source to the fabric surface).

While the use of an automatic system, such as that described in general terms above, is obviously desirable in a modern commercial manufacturing facility handling large quantities of fabric pieces, it is clearly not essential. The flipping could be done manually by a human being who is situated along as assembly line and who reacts to an audible or visible signal from a comparator (or even from another person reading the light intensity measurements directly off the sensors) to either flip a fabric piece or let it pass down the assembly line.

What is claimed is:

1. A method for determining the difference in sides of woven fabric comprising the following steps:
   (a) Situating one or more light sources so as to project the light beams at oblique angles to the said fabric in a first position:
   (b) With respect to each such light source, situating a sensor capable of measuring the intensity of said light beam as reflected off said fabric from said corresponding light source;
   (c) Measuring the intensity of the reflected light beam and comparing said intensity with pre-determined calibrations resulting from prior said measurements of the intensities of reflections of said light beams on the respective sides of similar fabric; and
   (d) Passing said fabric to a second position or flipping it to the opposite side and passing it to a second position, depending on the comparison made in (c) above which indicates the side orientation of said fabric.

2. A method as described in claim 1 wherein the light projected from said light source is infrared.

3. A method as described in claim 1 wherein said sensor is a photoelectric receiver capable of measuring intensities of reflected light.

4. A method as described in claim 1 wherein the intensity of reflected light is compared with pre-determined calibrations by means of an electronic differential amplifier.

5. A method as described in claim 4 wherein multiple comparisons of reflected light intensities are made at different points on one or both surfaces of said fabric to reduce the possibility of error.

6. A method as described in claim 4 wherein the electronic differential amplifer produces different output signals depending on said comparison of light intensities, to activate a means used for passing said fabric or flipping said fabric to its opposite side, depending upon which output signal is received by said means.

7. A method as described in claim 1 wherein a computer or programmable controller is used to produce different output signals, depending in part on said comparison of light intensities, to activate a means used for passing or flipping said fabric to its opposite side, depending upon which output signal is received by said means.

8. A method as described in claim 2 wherein said sensor is a photoelectric receiver capable of measuring intensities of the reflected infrared light.

9. A method as described in claim 2 wherein the intensity of the reflected infrared light is compared with pre-determined calibrations by means of an electronic differential amplifier.

10. A method as described in claim 9 wherein multiple comparisons of reflected infrared light intensities are made at different points on one or both surfaces of said fabric to reduce the possibility of error.

11. A method as described in claim 9 wherein the electronic differential amplifier produces different output signals, depending on said comparison of infrared light intensities, to activate a means used for passing said fabric or flipping said fabric to its opposite side, depending upon which output signal is received by said means.

12. A method as described in claim 1 wherein the intensity of reflected light is compared with pre-determined calibrations by means of a voltage comparator.

13. A method as described in claim 12 wherein the voltage comparator produces different output signals, depending on said comparison of light intensities, to activate a means used for passing said fabric or flipping said fabric to its opposite side, depending upon which output signal is received by said means.

14. A method as described in claim 2 wherein the intensity of the reflected infrared light is compared with pre-determined calibrations by means of a voltage comparator.

15. A method as described in claim 14 wherein the voltage comparator produces different output signals, depending on said comparison of light intensities, to activate a means used for passing said fabric or flipping said fabric to its opposite side, depending upon which output signal is received by said means.

16. A method for determining the difference in sides of woven fabric comprising the following steps:
   (a) Situating one or more light sources so as to project the light beams at oblique angles to the said fabric in a first position;
   (b) Situating at least two differently oriented sensors capable of measuring respective intensities of different scattering patterns of said light beams as reflected off said fabric;
   (c) Measuring relative intensities of the different reflected scattering patterns from said light source or sources and comparing said relative intensities; and
   (d) Passing said fabric to a second position or flipping it to the opposite side and passing it to a second position, depending on the comparison made in (c) above which indicates the side orientation of said fabric.

17. A method as described in claim 16 wherein the light projected from said light sources is infrared.

18. A method as described in claim 16 wherein said sensors are photoelectric receivers capable of measuring intensities of reflected light.

19. A method as described in claim 16 wherein the relative intensities of reflected light indicated by said differently oriented sensors are compared to each other by means of an electronic differential amplifier.

20. A method as described in claim 19 wherein multiple comparison of reflected light intensities are made at different points on one or both surfaces of said fabric to reduce the possibility of error.

21. A method as described in claim 19 wherein the electronic differential amplifier produces different output signals, depending on said comparison of light intensities, to activate a means used for passing said fabric or flipping said fabric to its opposite side, depending upon which output signal is received by said means.

22. A method as described in claim 16 wherein a computer or programmable controller is used to produce different output signals, depending in part on said comparison of light intensities, to activate a means used for passing said fabric or flipping said fabric to its opposite side, depending upon which output signal is received by said means.

23. A method as described in claim 17 wherein said sensors are photoelectric receivers capable of measuring intensities of the reflected infrared light.

24. A method as described in claim 17 wherein the relative intensities of reflected infrared light indicated by said differently oriented sensors are compared with each other by means of an electronic differential amplifier.

25. A method as described in claim 24 wherein multiple comparisons of reflected infrared light intensities are made at different points on one or both surfaces of said fabric to reduce the possibility of error.

26. A method as described in claim 24 wherein the electronic differential amplifier produces different output signals, depending on said comparison of infrared light intensities, to activate a means used for passing said fabric or flipping said fabric to its opposite side, depending upon which output signal is received by said means.

27. A method as described in claim 16 wherein relative intensities of reflected light indicated by said differently oriented sensors are compared to each other by means of a voltage comparator.

28. A method as described in claim 27 wherein multiple comparisons of reflected light intensities are made at different points on one or both surfaces of said fabric to reduce the possibility of error.

29. A method as described in claim 27 wherein the voltage comparator produces different output signals, depending on said comparison of light intensities, to activate a means used for passing said fabric or flipping said fabric to its opposite side, depending upon which output signal is received by said means.

30. A method as described in claim 17 wherein the relative intensities of reflected infrared light indicated by said differently oriented sensors are compared with each other by means of a voltage comparator.

31. A method as described in claim 30 wherein multiple comparisons of reflected infrared light intensities are made at different points on one or both surfaces of said fabric to reduce the possibility of error.

32. A method as described in claim 30 wherein the voltage comparator produces different output signals, depending on said comparison of infrared light intensities, to activate a means for passing said fabric or flipping said fabric to its opposite side, depending upon which output signal is received by said means.

* * * * *